US012559214B2

(12) United States Patent
Yu et al.

(10) Patent No.: US 12,559,214 B2
(45) Date of Patent: Feb. 24, 2026

(54) FISH-LIKE SHAPE ROBOTIC DEVICE

(71) Applicant: City University of Hong Kong, Hong Kong (HK)

(72) Inventors: Xinge Yu, Hong Kong (HK); Dengfeng Li, Hong Kong (HK); Jingkun Zhou, Hong Kong (HK); Xingcan Huang, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 495 days.

(21) Appl. No.: 18/170,566

(22) Filed: Feb. 17, 2023

(65) Prior Publication Data

US 2024/0278888 A1    Aug. 22, 2024

(51) Int. Cl.
| | |
|---|---|
| *B63G 8/04* | (2006.01) |
| *B63G 8/00* | (2006.01) |
| *B63G 8/08* | (2006.01) |
| *G01N 33/18* | (2006.01) |

(52) U.S. Cl.
CPC .............. *B63G 8/001* (2013.01); *B63G 8/04* (2013.01); *B63G 8/08* (2013.01); *G01N 33/1813* (2013.01); *G01N 33/182* (2013.01); *G01N 33/1826* (2013.01); *G01N 33/1886* (2013.01); *B63G 2008/002* (2013.01)

(58) Field of Classification Search
CPC . B63G 8/00; B63G 8/001; B63G 8/04; B63G 8/08; G01N 33/1813; G01N 33/182; G01N 33/1826; G01N 33/1886
USPC ......................................................... 114/337
See application file for complete search history.

(56) References Cited

FOREIGN PATENT DOCUMENTS

| | | | | |
|---|---|---|---|---|
| CN | 107144677 A | * | 9/2017 | ............. G01S 19/01 |
| KR | 20190072225 A | * | 6/2019 | .............. B63G 8/24 |

OTHER PUBLICATIONS

Guorui Li et al. Self-powered soft robot in the Mariana Trench. Nature. 591, 66-71 (2021).
T. Bujard et al. A resonant squid-inspired robot unlocks biological propulsive efficiency. Science Robotics. 6, eabd2971 (2021).
(Continued)

*Primary Examiner* — Lars A Olson
(74) *Attorney, Agent, or Firm* — Idea Intellectual Limited; Sam T. Yip

(57) ABSTRACT

A fish-like shape robotic device includes a fish-like shape carrier portion, a vibrable tail portion, a wireless power receiving module, a driving module, and at least one functional sensor. The fish-like shape carrier portion includes a head portion and a pair of side portions. The wireless power receiving module is configured to receive a wireless power and disposed on the vibrable tail portion and the side portions. The driving module is disposed on the vibrable tail portion, in which the wireless power receiving module transmits the wireless power to the driving module, such that the driving module enables the vibrable tail portion vibrate. The at least one functional sensor is disposed at the head portion and configured to sense a characteristic of an aquatic environment, or detect a living body or a bio-like structure in the aquatic environment, so as to obtain at least one sensing electrical signal.

20 Claims, 14 Drawing Sheets
(6 of 14 Drawing Sheet(s) Filed in Color)

(56) References Cited

OTHER PUBLICATIONS

F. A. & Co.KG, BionicFinWave: Underwater robot with unique fin drive. https://www.festo.com/net/it-it_it/SupportPortal/Files/504366/Festo_BionicFinWave_en.pdf (2019).

F. Berlinger et al. Implicit coordination for 3D underwater collective behaviors in a fish-inspired robot swarm. Science Robotics. 6, eabd8668 (2021).

V. I. Ogurtsov et al. Development of an Integrated Electrochemical Sensing System to Monitor Port Water Quality Using Autonomous Robotic Fish (Elsevier, 2014; http://dx.doi.org/10.1016/B978-0-08-096532-1.01312-1), vol. 13.

R. K. Katzschmann et al. Exploration of underwater life with an acoustically controlled soft robotic fish. Science Robotics. 3, eaar3449 (2018).

Xinge Yu et al. Skin-integrated wireless haptic interfaces for virtual and augmented reality. Nature. 575, 473-479 (2019).

Q. Zhong et al. Tunable stiffness enables fast and efficient swimming in fish-like robots. Science Robotics. 6, eabe4088 (2021).

COVID-19. https://news.google.com/covid19/map?hl=zh-HK&mid=%2Fm%2F02j71&gl=HK&ceid=HK%3Azh-Hant (2022).

* cited by examiner

FISH-LIKE SHAPE ROBOTIC DEVICE

COPYRIGHT NOTICE

FIELD OF THE INVENTION

The present invention generally relates to a robotic device, and, more particularly to a fish-like shape robotic device for monitoring/sensing characteristics of aquatic environment (e.g., temperature, or liquid quality) and detecting living body or bio-like structure (e.g., virus) therein.

BACKGROUND OF THE INVENTION

The aquatic environment is a large portion of the earth's surface and exploration of aqueous settings is extremely important. Due to adverse or dangerous conditions in aquatic environments, humans are unable to readily gain access; consequently, robot exploration becomes a necessary alternative.

However, some large-scale robots are particularly constrained in narrow environments, so it is necessary but challenging to dramatically reduce the robot size while retaining multiple intelligent functions. Besides, conventional robots are usually driven by electricity power provided by batteries. Nevertheless, the configuration of the batteries may pose some limitations for the miniaturization of the robots, for example a significant burden to lightweight soft robots, a limited operation life, and an increased moving resistance. Therefore, there is a need to develop a new robot to address the aforesaid issues.

SUMMARY OF THE INVENTION

It is an objective of the present invention to provide a fish-like shape robotic device to solve the aforementioned technical problems.

In accordance with a first aspect of the present invention, the fish-like shape robotic device includes a fish-like shape carrier portion, a vibrable tail portion, a wireless power receiving module, a driving module, and at least one functional sensor. The fish-like shape carrier portion includes a head portion and a pair of side portions extending from two opposite sides of a bottom of the head portion, respectively. The vibrable tail portion connects to the head portion and located between the pair of side portions. The wireless power receiving module is configured to receive a wireless power and disposed on the vibrable tail portion and the side portions. The driving module is electrically coupled to the wireless power receiving module and disposed on the vibrable tail portion, in which the wireless power receiving module transmits the wireless power to the driving module, such that the driving module enables the vibrable tail portion vibrate. The at least one functional sensor is disposed at the head portion and configured to sense a characteristic of an aquatic environment, or detect a living body or a bio-like structure in the aquatic environment, so as to obtain at least one sensing electrical signal.

In accordance with one embodiment of the present invention, center of mass of the fish-like shape robotic device is matched to centroid of the fish-like shape robotic device.

In accordance with another embodiment of the present invention, the at least one functional sensor includes a plurality of chemical ion sensors for detecting $NH_4^+$ ion and $Cl^-$ ion, and a biosensor for sensing the SARS-CoV-2 virus.

In accordance with yet embodiment of the present invention, the fish-like shape robotic device is driven by electromagnetic force.

Based on the above, in the embodiments of the present disclosure, shape of the robotic device adopts a biomimetic design, such as fish-like shape design, so as to adapt the movement in the aquatic environment. The robotic device is provided with a wireless power receiving module for receiving radio frequency (RF) wireless power, such that the robotic device may be driven by the wireless power instead of using batteries. Therefore, the robotic device may have a small volume and may swim in a confined space. In addition, as the fish-like shape robotic device move in an aquatic environment, at least one functional sensor thereof may sense at least one parameters of the aquatic environment, such as water temperature, or ions concentration. In other embodiments, the functional sensor may detect living body or bio-like structure (e.g., severe acute respiratory syndrome coronavirus 2 (SARS-CoV-2) virus).

BRIEF DESCRIPTION OF THE DRAWINGS

The patent or application file contains at least one drawing executed in color. Copies of this patent application with color drawing(s) will be provided by the Office upon request and payment of necessary fee.

Embodiments of the invention are described in more details hereinafter with reference to the drawings, in which.

DETAILED DESCRIPTION

In the following description, a fish-like shape robotic device and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1A:
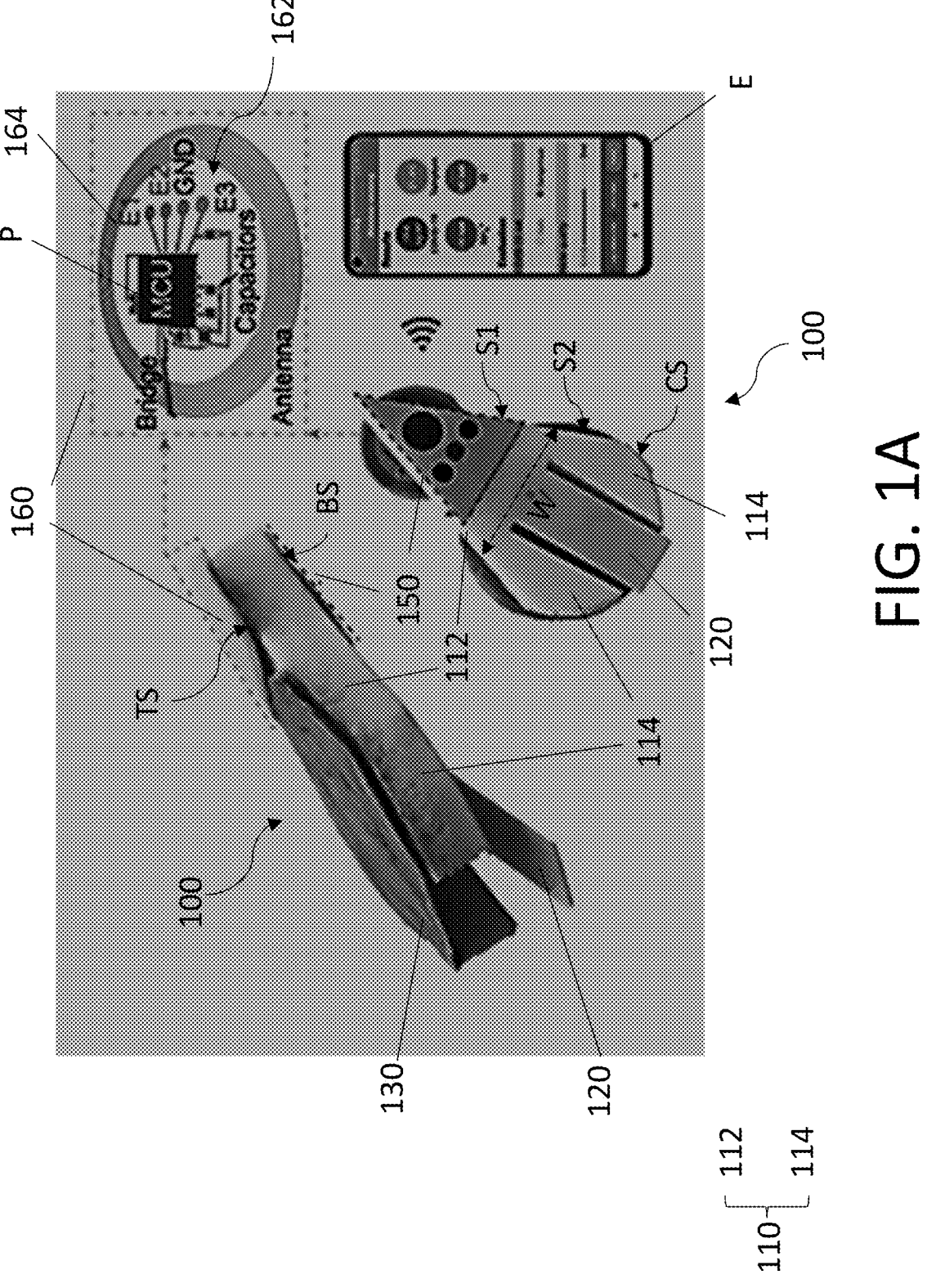
FIG. 1A depicts a side view and a bottom view of a fish-like shape robotic device with a mobile phone interface.
Figure 1B:
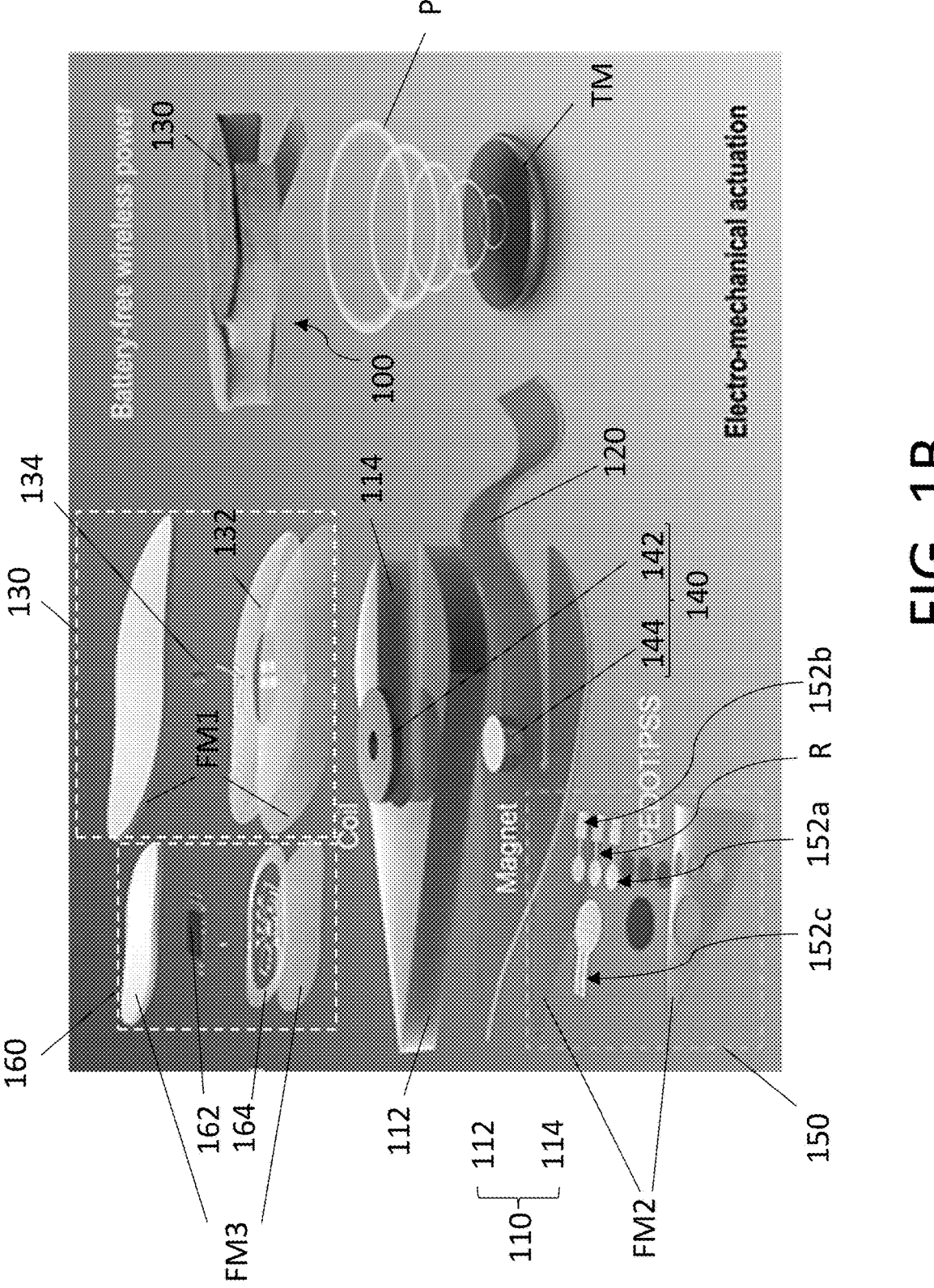
FIG. 1B depicts an exploded view of the fish-like shape robotic device in the FIG. 1A.

FIG. 1A depicts a side view and a bottom view of a fish-like shape robotic device 100 with a mobile phone interface. FIG. 1B depicts an exploded view of the fish-like shape robotic device 100 in the FIG. 1A.

Referring to FIGS. 1A and 1B, in the embodiment, a robotic device 100 adopts a biomimetic design, such as a fish-like shape design, such that the robotic device 100 may be adapt in an aquatic environment (such as water). In detail, the robotic device 100 includes a carrier portion 110, a vibrable tail portion 120, a wireless power receiving module 130, a driving module 140, a sensing module 150 including a plurality of functional sensors 152a,152b,152c, and a wireless sensing data reading module 160. The aforesaid elements and the arrangement therebetween will be fully described as follows.

The carrier portion 110 may have a fish-like shape. The carrier portion 110 includes a head portion 112 and a pair of side portions 114. The pair of side portions 114 extend from two opposite sides of a bottom of the head portion 112, respectively. A side surface S1 of the head portion 112 is connected to a side surface S2 of the side portion 114, and both of them collectively form a greater, continuous, and inclined side surface. A bottom of the side portions 114 may have a convex surface connected to the side surface S2. Overall, the carrier portion 110 has a width W gradually increasing and then decreasing from a top of the carrier portion 110 (e.g., a top of the head portion 112) to a bottom of the carrier portion 110 (e.g., a bottom of the side portion 114). Such a shape design is advantageous to assist the robotic device 100 swim/move in an aquatic environment.

The vibrable tail portion 120 is connected to the head portion 112, and extends from the bottom of the head portion 112. The vibrable tail portion 120 is located/sandwiched between the pair of side portions 114. The vibrable tail portion 120 is spaced apart from the side portions 114, so that the vibrable tail portion 120 may rotate freely. The shape of the vibrable tail portion 120 may be, for example, rectangular, and the present disclosure is not limited thereto.

In some embodiments, the exemplary materials of the carrier portion 110 may be elastic/soft materials, and the density of the used elastic/soft materials is less than that of water. For example, in an embodiment, the elastic/soft materials may be aerogel silicone foam, which is prepared by curing a mixture of aerogel powder and polydimethylsiloxane (PDMS), and the present disclosure is not limited thereto.

In some embodiments, the exemplary materials of the vibrable tail portion 120 may be elastic/soft materials, for example, silicone.

Figure 2B:
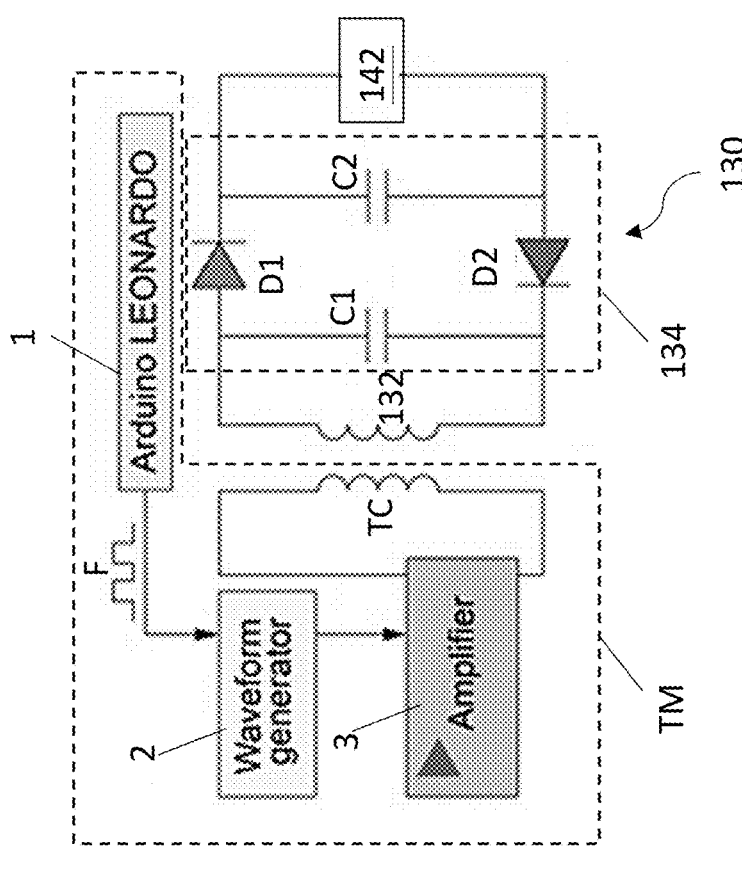
FIG. 2B depicts a circuit diagram of the wireless power transmitting module and the wireless power receiving module.
Figure 2A:
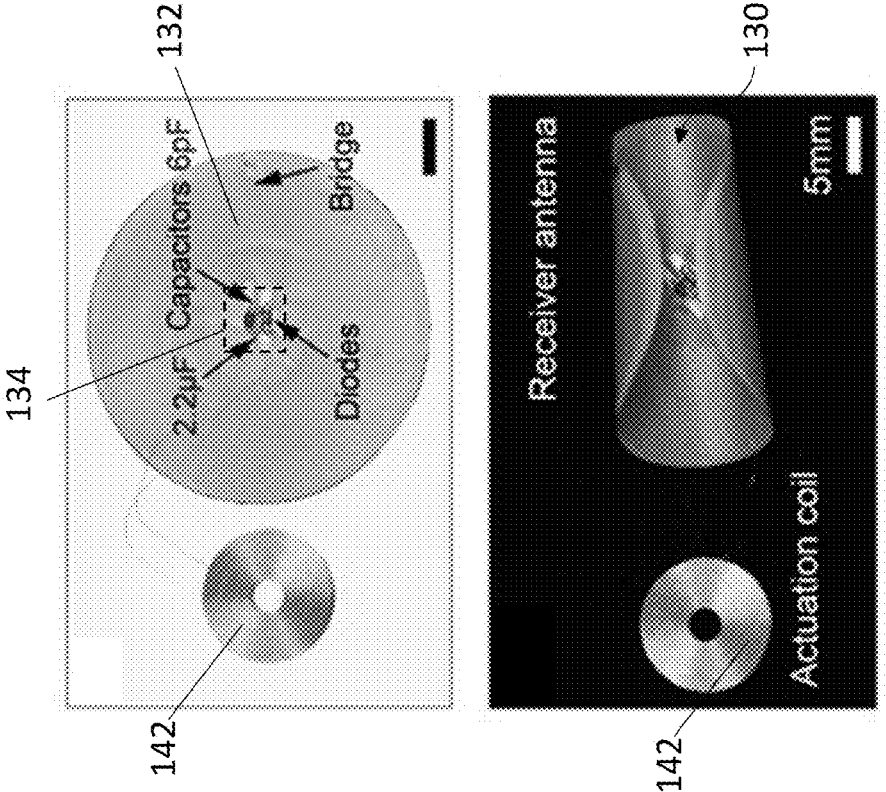
FIG. 2A shows an exterior of the wireless power receiving module and an actuation coil of the driving module.
Figures 2C, 2D:
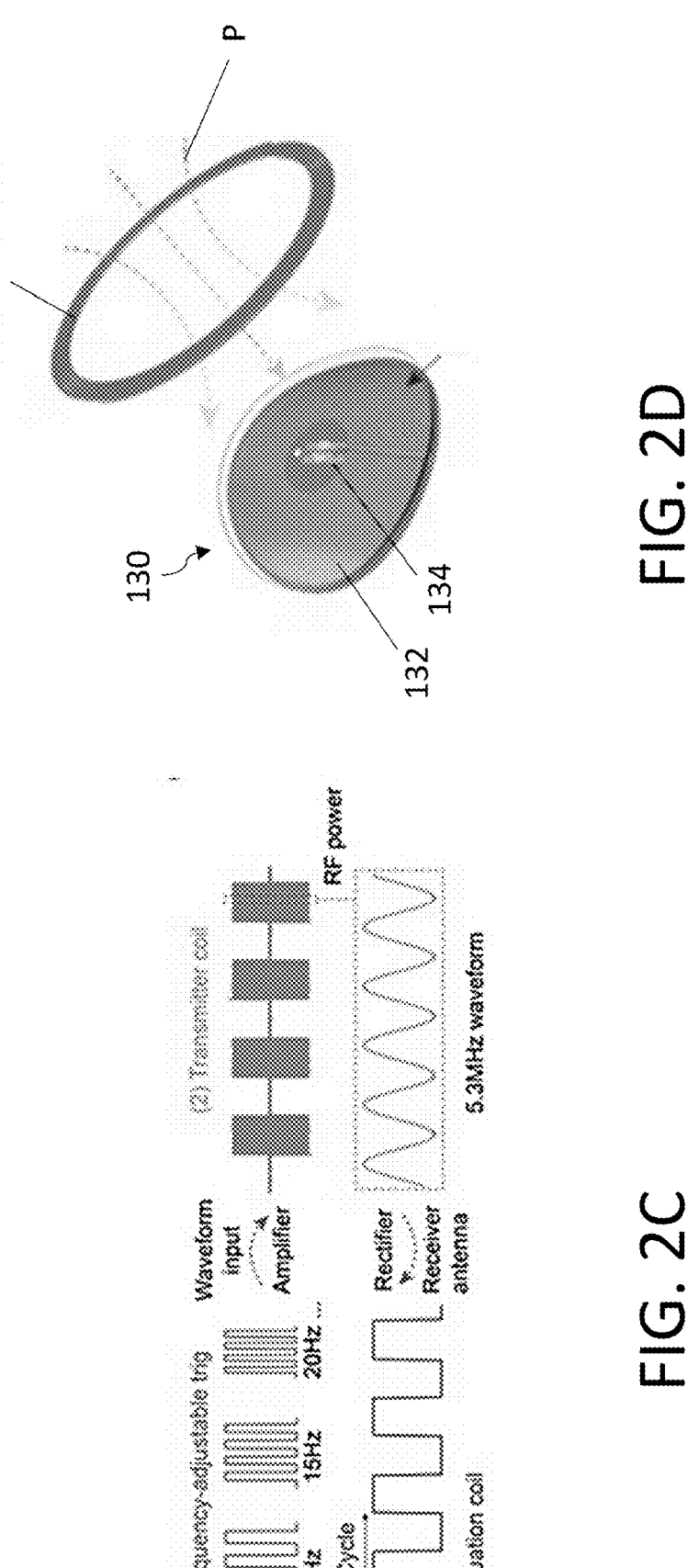
FIG. 2C depicts a process flow of a wireless actuation process according to an embodiment of the present disclosure.
FIG. 2D depicts a schematic diagram of using a wireless power transmitting module to power a receiver antenna of the wireless power receiving module.

FIG. 2A shows an exterior of the wireless power receiving module 130 and an actuation coil 142 of the driving module 140. FIG. 2B depicts a circuit diagram of the wireless power transmitting module TM and the wireless power receiving module 130. FIG. 2C depicts a process flow of a wireless actuation process according to an embodiment of the present disclosure. FIG. 2D depicts a schematic diagram of using a wireless power transmitting module TM to power a receiver antenna RA of the wireless power receiving module 130.

In order to make the robotic device 100 be more adaptable to a narrow space/environment, the robotic device 100 adopts a battery-free design. To be more specific, the robot device 100 is wirelessly powered through the wireless power receiving module 130 instead of using battery. Thus, the robotic device 100 can have a smaller volume and can move in a narrow environment/space. The detailed configuration of the wireless power receiving module 130 and the driving module 140 will be fully described as follows.

Referring to FIGS. 1A and 1B again, specifically, the wireless power receiving module 130 is disposed on (or covers) the vibrable tail portion 120, the side portions 114 and a part of the head portion 112. The wireless power receiving module 130 is vertically spaced apart from the vibrable tail portion 120 but makes contact with the side portions 114 and the part of the head portion 112. Such a configuration can make the wireless power receiving module 130 to be carried by the carrier portion 110 and would not affect the motion of the vibrable tail portion 120.

Referring to FIGS. 1B and 2B again, the wireless power receiving module 130 includes a plurality of flexible and waterproof thin films FM1, a receiver antenna 132, and a circuit 134 including a plurality of capacitors C1, C2, a plurality of diodes D1, D2. In some embodiments, the exemplary materials of the thin films FM1 may be, for example, polyimide (PI), and the present disclosure is not limited thereto. The receiver antenna 132 and the circuit 134 are disposed in between ((or sandwiched between) the two flexible and waterproof thin films FM1, such that the receiver antenna 132 and the circuit 134 can be protected by the thin films FM1.

In some embodiments, the exemplary materials of the receiver antenna 132 may be, for example, conductive material possessed with excellent ductility, such as copper or gold. Also, the thickness of the receiver antenna 132 is well controlled/formed, such that the receiver antenna 132 may be formed as a flexible/bendable receiver antenna 132 as shown in a lower part of FIG. 2A.

The driving module 140 is disposed directly under the wireless power receiving module 130. The driving module 140 is disposed on the vibrable tail portion 120. The driving module 140 includes an actuation coil 142, and a magnet element 144. The actuation coil 142 of the driving module 140 is disposed above and adjacent to the magnet element 144. The actuation coil 142 is carried and surrounded by the head portion 112, and side portions 114. The actuation coil 142 is electrically coupled to the receiver antenna 132 through the circuit 134 as shown in the FIGS. 2A and 2B. The magnet element 144 is disposed at and makes contact with a top of the vibrable tail portion 120. In some embodiments, the actuation coil 142 may be, for example, a 1200-turn circular coil, and the present disclosure is not limited thereto. In some embodiments, the magnet element 144 may be, for example, a magnet, and the present disclosure is not limited thereto.

Referring to FIG. 2B, the two capacitors C1, C2 are connected in parallel with the actuation coil 142 of the driving module 140. In some embodiments, a capacitance of the capacitor C1 may be, for example, 6 pF. In some embodiments, a capacitance of the capacitor C2 may be, for example, 2.2 μF. Values of the capacitances of the capacitors C1, C2 can be determined according to device requirements, and the present disclosure is not limited thereto.

An anode of the diode D1, the capacitor C1, and the receiver antenna 132 are electrically connected to the same node. A cathode of the diode D1, the capacitor C1, and the actuation coil 142 are electrically connected to the same node. An anode of the diode D2, the capacitor C2, and the actuation coil 142 are electrically connected to the same node. A cathode of the diode D2, the capacitor C1, and the receiver antenna 132 are electrically connected to the same node. The diodes D1, D2 are electrically coupled in series in the circuit 134 to obtain a unidirectional output voltage.

Next, the power supply process and the actuation process of the robotic device 100 of the present disclosure will be fully described as follows.

First of all, in the present disclosure, a wireless power transmitting module TM is used/applied to generate/provide a wireless power P to drive the robotic device 100. Referring back to FIG. 2B again, the wireless power transmitting module TM includes an Arduino LEONARDO board 1, a waveform generator 2, an amplifier 3, and a transmitter coil TC.

Referring to FIGS. 2B and 2C, the step (1): the Arduino LEONARDO board 1 may generate and transmit a frequency-adjustable triggering signal F to the waveform generator 2. In some embodiments, the frequency-adjustable triggering signal F may be, for example, an adjustable square wave with frequency from 2.5 Hz to 40 Hz. The waveform generator 2 may be triggered by the frequency-adjustable triggering signal F, such that a sinewave voltage signal defined as input voltage signal at the MHz level is generated. In some embodiments, the sinewave voltage signal may be, for example, a 5.3 MHz sinewave voltage signal. Next, the sinewave voltage signal generated by the waveform generator 2 is amplified by the amplifier 3.

The step (2): then, the amplified sinewave voltage, which is served as a source of the wireless power P, is transmitted to/loaded onto the transmitter coil TC. After that, the wireless power P is transmitted/emitted wirelessly by the transmitter coil TC in a form of radio frequency (RF) electromagnetic fields, and then the receiver antenna 132 may collect/receive the wireless power P (the waveform thereof is shown in a step (2) of the FIG. 2C) in a non-contact manner.

The step (3): next, after the receiver antenna 132 receives the wireless power P, the wireless power P may be transmitted to the circuit 134, such that the circuit 134 can modify a waveform of the wireless power P. Then, the circuit 134 may output the modified wireless power P to the actuation coil 142. In detail, the two diodes D1, D2 in the circuit 134 may act as rectifiers, such that the wireless power P may be rectified by the diodes D1, D2. Furthermore, the capacitor C1 in the circuit 134 may adjust the resonant frequency of the receiver antenna 132, and the capacitor C2 may be used to stabilize the output voltage (i.e., modified wireless power P) loaded onto the actuation coil 142 of the driving module 140. Thus, an output voltage with a unilateral square-wave waveform may be generated/obtained, and may be loaded onto the actuation coil 142.

Figure 3:
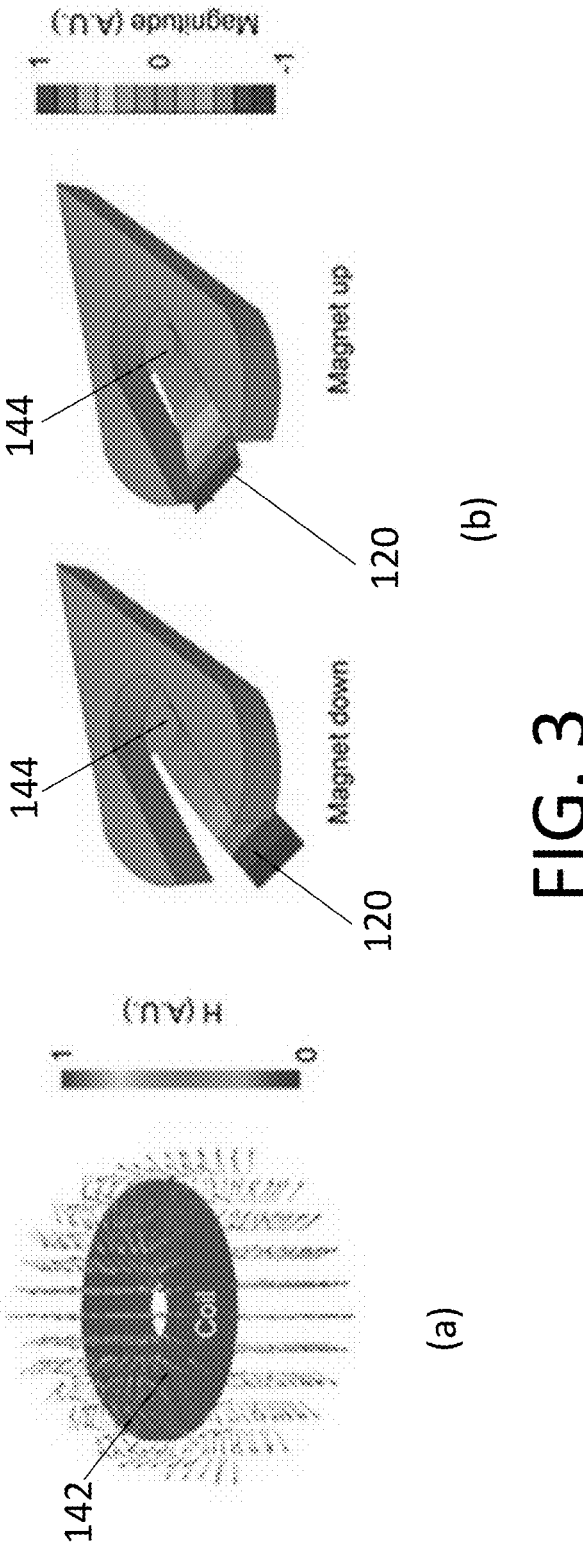
FIG. 3 shows simulation results of the magnetic field distribution of the actuation coil and vibration magnitude of the vibrable tail portion during the electro-mechanical actuation.
Figure 4:
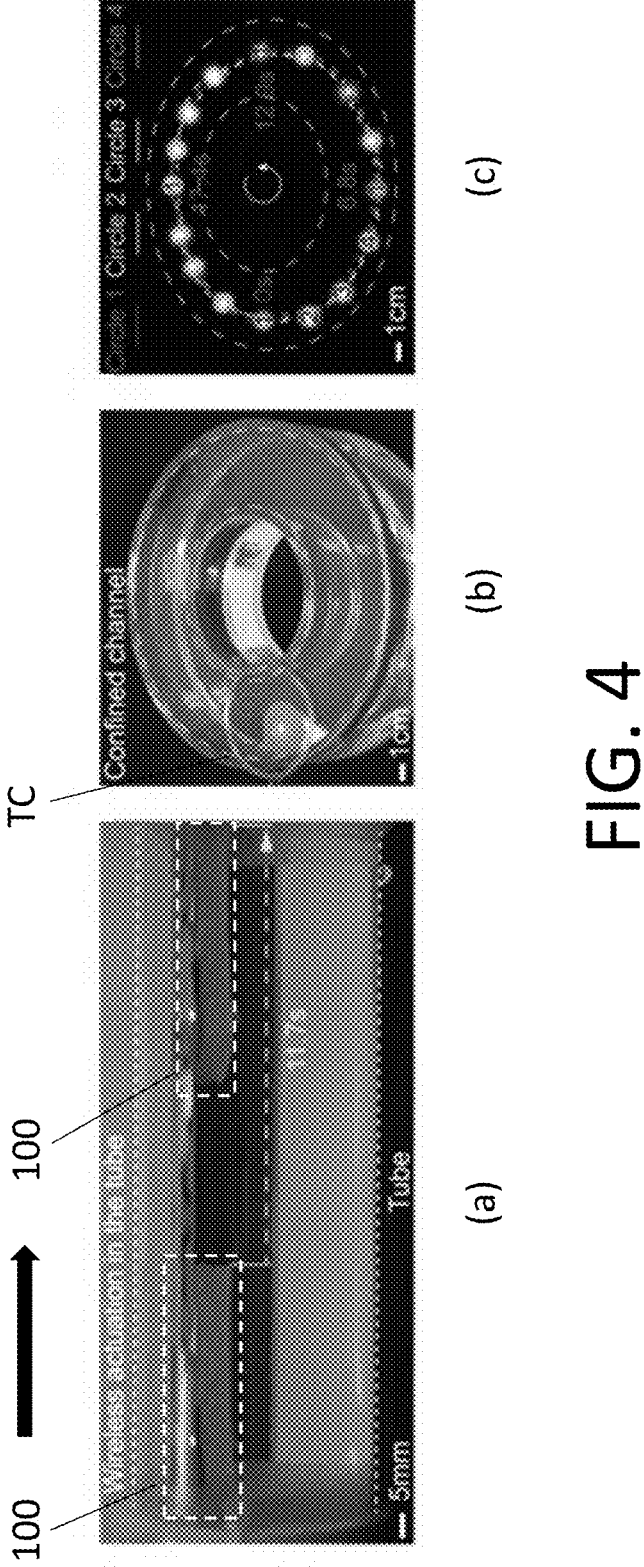
FIG. 4 shows the robotic device swimming in a closed tube.
Figure 5:
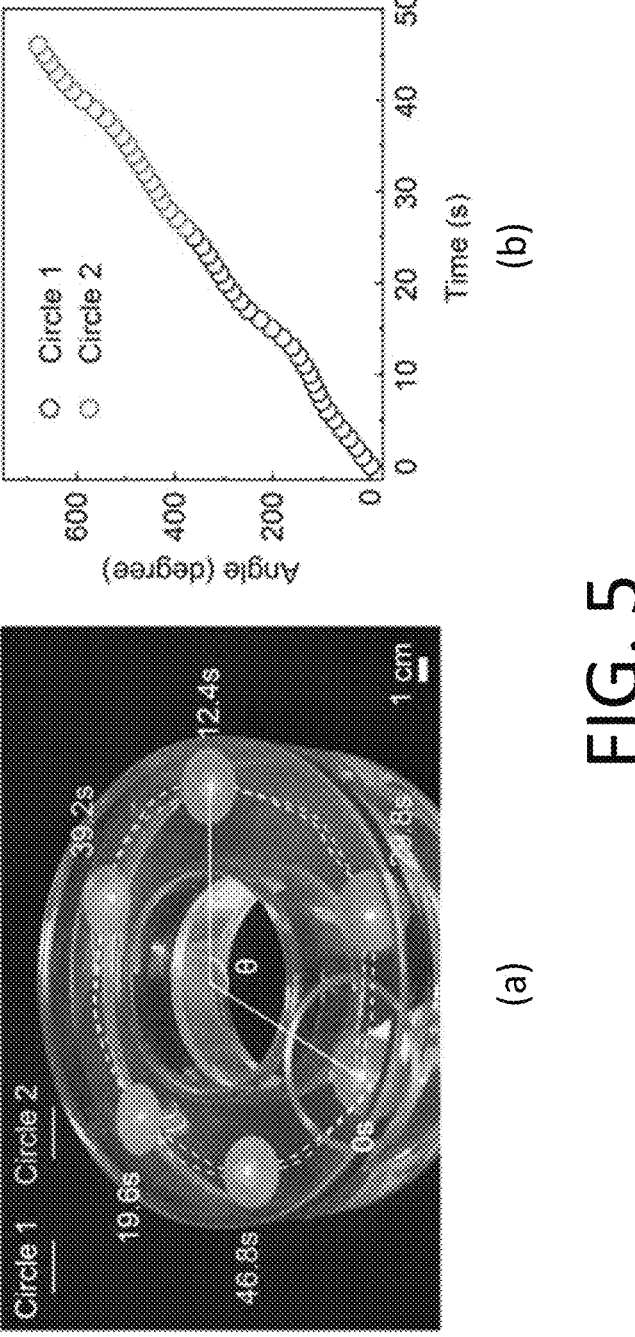
FIG. 5 shows position and timing of the robotic device in a circular confined pipe during the two laps around the circular closed pipe under the bright environment and the relationship between angle and time in two lap movements.

FIG. 3 shows simulation results of the magnetic field distribution of the actuation coil 142 and vibration magnitude of the vibrable tail portion 120 during the electromechanical actuation. FIG. 4 shows the robotic device swimming in a closed tube. FIG. 5 shows position and timing of the robotic device 100 in a circular confined pipe during the two laps around the circular closed pipe under the bright environment and the relationship between angle and time in two lap movements.

Referring to FIG. 3, the left part of FIG. 3 shows a simulation of the magnetic field distribution of the actuation coil 142. When the actuation coil 142 is loaded onto/powered by a direct current, a magnetic field may be generated by the actuation coil 142. The magnet element 144 below the actuation coil 142 may be attracted or repelled by the actuation coil 142 by Lorentz force. As the actuation coil 142 is loaded onto/powered by the aforesaid output voltage outputted by the circuit 134, an alternative/oscillating magnetic field would be generated by the actuation coil 142. Then, the actuation coil 142 generate a periodic Lorentz force with the oscillating magnetic field. Under the periodic Lorentz force, the magnet element 144 on the vibrable tail portion 120 would periodically oscillate up and down, such that the vibrable tail portion 120 of the robotic device 100 is enable to swing/vibrate. Thus, the soft robot swam forward in the water.

Referring to FIG. 4, when the robotic device 100 is placed in an aquatic environment, the oscillation motion of the vibrable tail portion 120 would achieve a forward propulsive movement through the interaction forces with fluid, and thus the robotic device 100 can swim in the aquatic environment/fluid. In this way, the robotic device 100 with the receiver antenna 132 could smoothly swim from one end to the other end of a pipe under the wireless power P provided by a transmitter coil TC as shown in (a) part of the FIG. 4.

To highlight its advantages in wireless actuation, the robotic device 100 may be placed in a circular confined pipe, in which the robotic device 100 may be repeatedly looped around therein as shown in (b) part of the FIG. 4 and in (a) part of the FIG. 5. In the bright environment, the position and angle of the moving robotic device 100 are recorded, and the linear relationship between angle and time shows that the swimming motion is uniform and stable as shown in (b) part of the FIG. 5. On the other hand, in the dark environment, the diodes D1 and D2 in the circuits 134 may be replaced with two light emitting diodes (LED), such that the robotic device 100 can be easily tracked with the flashing LED lights as shown in (c) part of the FIG. 4, in which (c) part of the FIG. 4 shows a four circles of circular motion with marked robotic device 100's positions by bright LEDs dots for each circle.

In short, in the present disclosure, through the aforesaid actuation process, the robotic device 100 may swim to many locations to obtain in-situ water/liquid information without taking the robot out. The wireless power P provided by the wireless power transmitting module TM may be wirelessly transferred to the robotic device 100 to actuate it swimming in the aquatic environment. The aforesaid swimming motion is derived from electromagnetic induction actuation that converts electrical energy into mechanical energy.

Referring back to the FIGS. 1A and 1B, the sensing module 150 is disposed at a bottom surface BS of the head portion 112. The sensing module 150 is configured to sense a characteristic of an aquatic environment where the robotic device 100 located, or detect a living body or a bio-like structure in the aquatic environment. The detailed configuration would be fully described as follows.

Figure 6B:
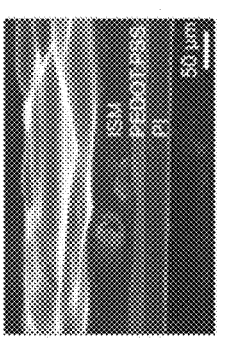
FIG. 6B depicts a schematic diagram of ions detection including $NH_4^+$ and $Cl^-$ ions and shows a cross-sectional scanning electron microscope (SEM) image of the functional sensor.
Figure 6B:
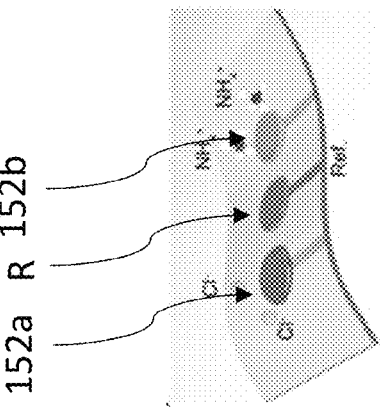
Figure 6A:
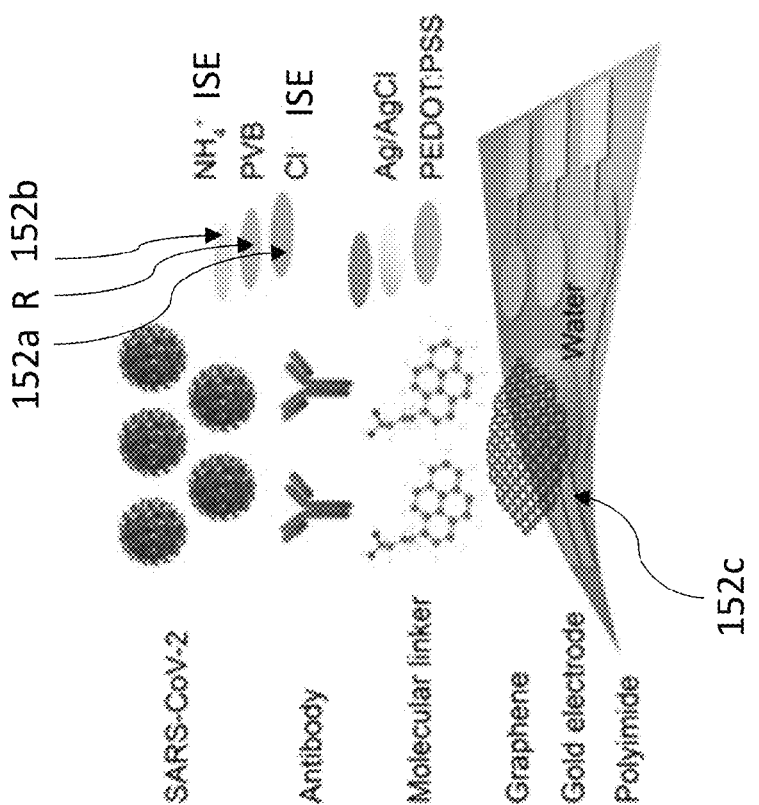
FIG. 6A depicts an exploded view of the sensing module.
Figure 6D:
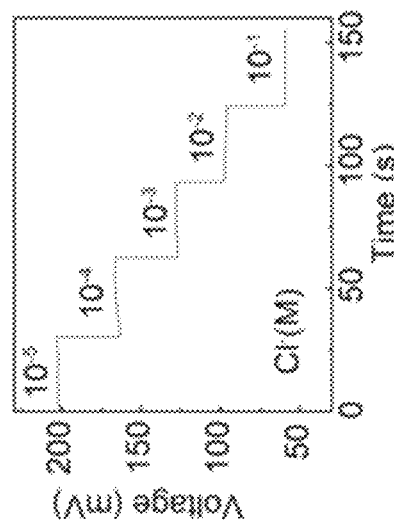
FIG. 6D shows a result of voltage response at different $Cl^-$ ion concentrations of the functional sensor for detecting $Cl^-$ ion.
Figure 6C:
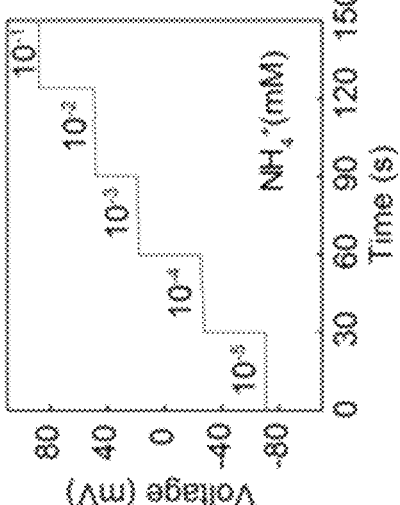
FIG. 6C shows a result of voltage response at different $NH_4^+$ ion concentrations of the functional sensor for detecting $NH_4^+$ ion.
Figure 7:
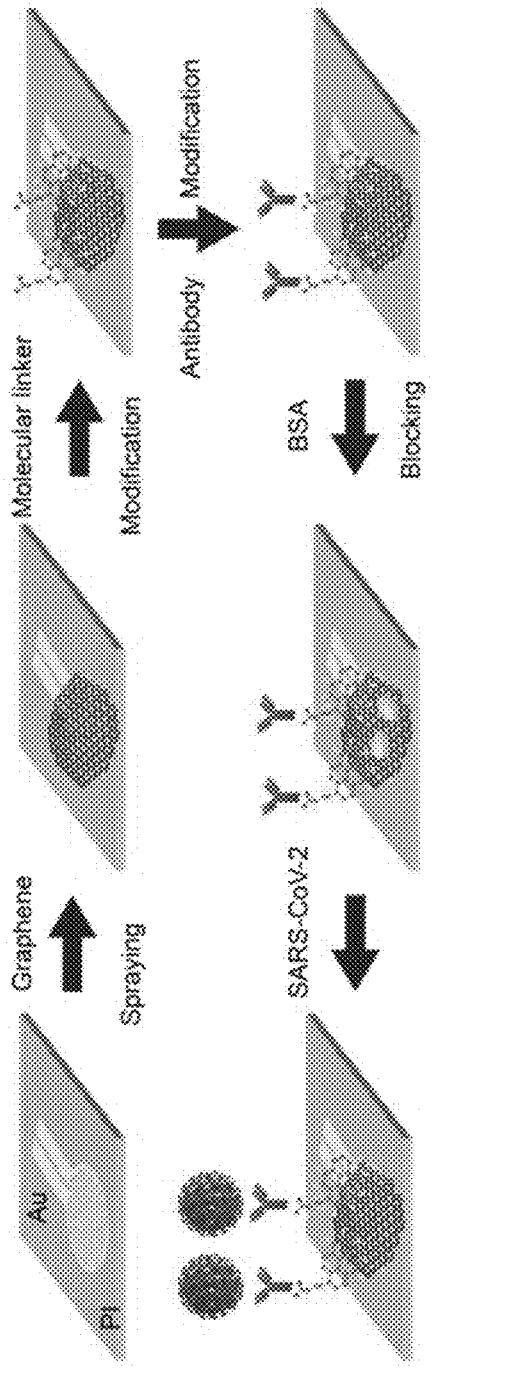
FIG. 7 depicts a manufacturing process of the functional sensor for sensing SARS-CoV-2 virus.
Figure 8:
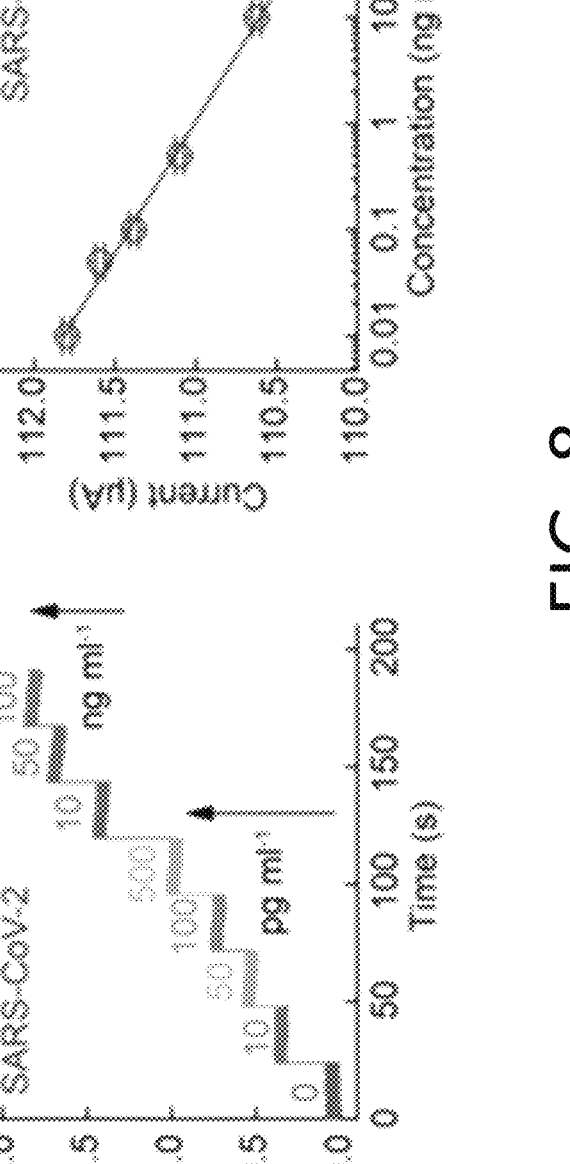
FIG. 8 shows results of percentage change in impedance values under different concentrations of SARS-CoV-2 virus solutions and linear relationship between virus concentration and current values.

FIG. 6A depicts an exploded view of the sensing module 150. FIG. 6B depicts a schematic diagram of ions detection including $NH_4^+$ and $Cl^-$ ions and shows a cross-sectional scanning electron microscope (SEM) image of the functional sensor. FIG. 6C shows a result of voltage response at different $NH_4^+$ ion concentrations of the functional sensor 152a for detecting $NH_4^+$ ion. FIG. 6D shows a result of voltage response at different $Cl-$ ion concentrations of the functional sensor 152b for detecting $Cl^-$ ion. FIG. 7 depicts a manufacturing process of the functional sensor 152c for sensing SARS-CoV-2 virus. FIG. 8 shows results of percentage change in impedance values under different concentrations of SARS-CoV-2 virus solutions and linear relationship between virus concentration and current values.

Referring to FIGS. 1B, 6A and 6B, in detail, the sensing module 150 includes a plurality of flexible and waterproof thin films FM2, a plurality of the functional sensors 152a, 152b, 152c, and a reference electrode R. In some embodiments, the exemplary materials of the thin films FM2 may be, for example, PI, and the present disclosure is not limited thereto. The functional sensors 152a, 152b, 152c and the reference electrode R are disposed in between ((or sandwiched between) the two flexible and waterproof thin films FM2, such that the functional sensors 152a, 152b, 152c and the reference electrode R can be protected by the thin films FM2.

In some cases, the robotic device 100 is aimed to monitor water quality of the aquatic environment and unconventional virus contamination. Since the concentrations of chlorine ions ($Cl^-$) and ammonium ions ($NH_4^+$) are an important quality indicator for drinking water, the functional sensor 152a is configured to sense, for example, chlorine ions ($Cl^-$) and the functional sensor 152b is configured to sense, for example, ammonium ions ($NH_4^+$). The functional sensors 152a and 152b serve as chemical sensors.

In addition, COVID-19 is still in pandemic worldwide. In addition to airborne respiratory inhalation and physical body contact with the virus, SASR-CoV-2 contamination of domestic water is a non-negligible spread route for COVID-19. Thus, the functional sensor 152c is configured to sense/detect bio-like structure, such as virus (e.g., SARS-CoV-2 virus). In other embodiments, the functional sensor 152c can detect a living body/organism, such as germs. The functional sensor 152c serves as a biosensor.

It should be noted that the aforesaid detected/tested substances (e.g., chlorine ions ($Cl^-$), ammonium ions ($NH_4^+$), or SARS-CoV-2 virus) are examples for satisfying a specific requirement. The functional sensors can detect other detected/test substances according to different requirements. The present disclosure is not limited thereto.

The detailed configuration of the sensing module 150 would be fully described as follows.

Referring to FIGS. 1B and 6A, the functional sensors 152a and 152b are disposed/formed on a lower flexible and waterproof thin film FM2 (see FIG. 1B). The functional sensors 152a, for sensing chlorine ions, includes a circular electrode, an interdigital electrode connected to the circular electrode, a poly(3,4-ethylenedioxythiophene) polystyrene sulfonate (PEDOT:PSS) layer, and an ion-selective electrode (ISE) for chlorine ions. The PEDOT:PSS layer is formed/disposed on the circular electrode. The ISE is formed/disposed on the PEDOT:PSS layer.

Similarly, the functional sensors 152b, for sensing ammonium ions, includes a circular electrode, an interdigital electrode connected to the circular electrode, a poly(3,4-ethylenedioxythiophene) polystyrene sulfonate (PEDOT: PSS) layer, and an ion-selective electrode (ISE) for ammonium ions. The PEDOT:PSS layer is formed/disposed on the circular electrode. The ISE is formed/disposed on the PEDOT:PSS layer.

The reference electrode R is located between the two functional sensors 152a and 152b. The reference electrode R includes a circular electrode, an interdigital electrode connected to the circular electrode, a Ag/AgCl layer is disposed/formed on the middle circular electrode and dropped with polyvinyl butyral (PVB) reference cocktail to form the reference electrode R.

By the configuration of the functional sensors 152a, 152b and the reference electrode R, the sensing module 150 may sense the ions-induced electrochemical potential difference between the corresponding function sensor 152a (or 152b) and the reference electrode R. Thus, the sensing module 150 can sense the concentration of $NH_4^+$ and $Cl^-$ ions as shown in the FIG. 6B. In some embodiments, the functional sensor 152a, for detecting $NH_4^+$ ions, exhibits good linearity in the electrolyte solutions with naturally relevant concentration concentrations from $10^{-5}$ M to $10^{-1}$ M as shown in the FIG. 6C. The functional sensor 152b, for detecting $Cl^-$ ions, also exhibits good linearity in the electrolyte solutions with naturally relevant concentration concentrations from $10^{-5}$ M to $10^{-1}$ M as shown in the FIG. 6D.

Referring to FIG. 6A, the functional sensor 152c is disposed/formed on a lower flexible and waterproof thin film FM2 (see FIG. 1B). Referring to FIG. 6A, the functional sensors 152c, for sensing SARS-CoV-2 virus, includes an interdigital electrode, a graphene layer, a molecular linker layer (e.g., 1-Pyrenebutyric acid (PBA), a blocking layer (e.g., Bovine serum albumin (BSA)), and antibodies of a specific virus (e.g., SARS-CoV-2 virus).

Referring to FIG. 7, first of all, an interdigital electrode is formed on/over/above the PI film. Then, a graphene layer is formed on/over/above the interdigital electrode. Next, a molecular linker layer is formed on/over/above the graphene layer to modify the graphene layer. Thereafter, a blocking layer is formed on/over/above the modified graphene layer using BSA. Finally, antibodies of SARS-CoV-2 virus are formed on/over/above the modified graphene layer for capturing antigens of SARS-CoV-2. The antibody binding to SARS-CoV-2 spike protein would cause the impedance change of the functional sensor 152c, which enables this label-free immune sensor to monitor the concentration of SARS-CoV-2 virus. Referring to the FIG. 8, the functional sensor 152c shows excellent sensing ability with high sensitivity and good linearity. Benefiting from the advanced structural design and the good conductivity of graphene film, there would be obvious impedance changes on the electrode even for a SARS-CoV-2 concentration as low as 10 pg/mL. Because of the large surface area and good biocompatibility of the graphene film, enough amounts of antibodies could be modified on the electrode to achieve an extensive detection range from 10 pg/mL to 100 ng/mL with good linearity.

Referring back to the FIGS. 1A and 1B, the wireless sensing data reading module 160 is disposed on a top surface TS of the head portion 112 of the carrier portion 110. The wireless sensing data reading module 160 includes a plurality of flexible and waterproof thin films FM3, a near field communication (NFC) circuit 162, and a transmitter antenna 164. In some embodiments, the exemplary materials of the thin films FM3 may be, for example, PI, and the present disclosure is not limited thereto. The NFC circuit 162 and the transmitter antenna 164 are disposed in between ((or sandwiched between) the two flexible and waterproof thin films FM3, such that the NFC circuit 162, the transmitter antenna 164 can be protected by the thin films FM3.

In some embodiments, the exemplary materials of the transmitter antenna 164 may be, for example, conductive material possessed with excellent ductility, such as copper or gold. Also, the thickness of the transmitter antenna 164 is well controlled/formed, such that the transmitter antenna 164 may be formed as a flexible/bendable transmitter antenna 164.

Figure 9:
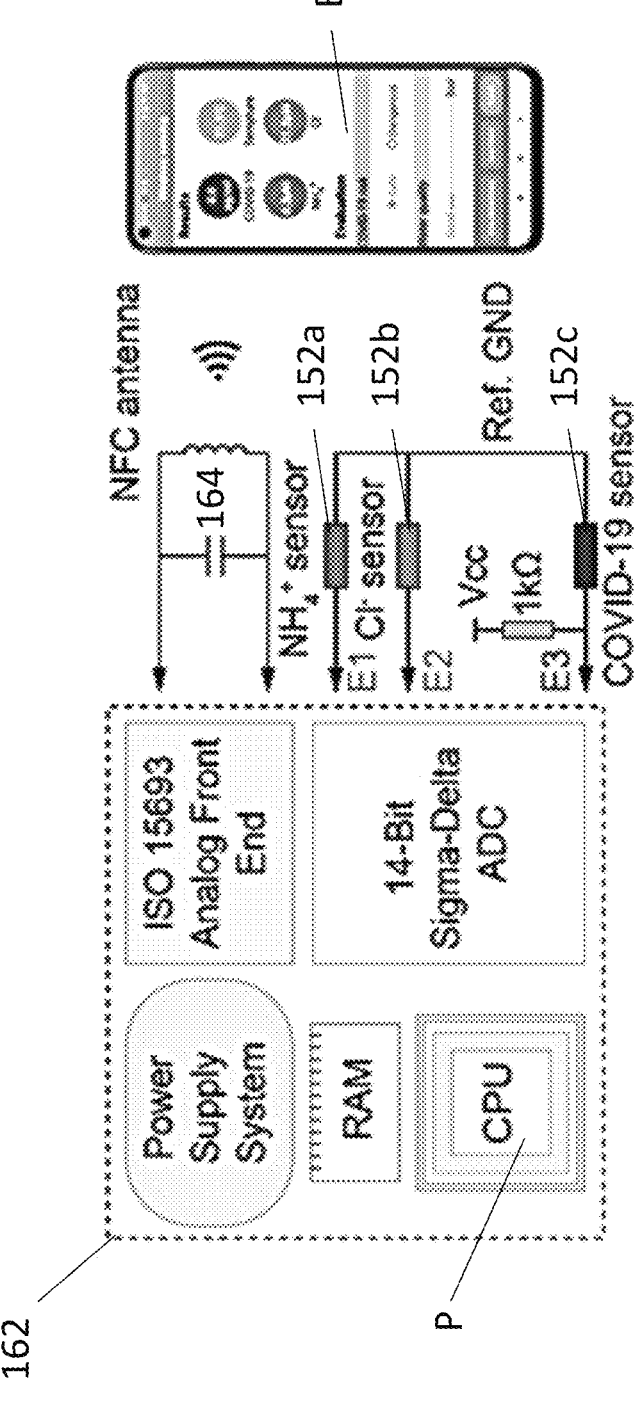
FIG. 9 depicts a circuit logic diagram and a mobile phone interface for wireless sensing.

FIG. 9 depicts a circuit logic diagram and a mobile phone interface for wireless sensing.

Referring to FIG. 9, in detail, the NFC circuit 162 includes a controller P, a plurality of conductive pads E1, E2, E3, an analog-to-digital converter (ADC) and a temperature sensor (not shown). In some embodiments, the controller P can be microcontroller unit (MCU). The NFC circuit 162 can be electrically coupled to the functional sensors 152a, 152b, 152c of the sensing modules 150 respectively through the conductive pads E1, E2, E3, and thus each of the functional sensors 152a, 152b, 152c can send a corresponding sensing signal to the ADC of the NFC circuit 162. Also, the temperature sensor can sense temperature of an environment where the robotic device 100 located, and then generate a temperature sensing signal. The ADC can convert the corresponding sensing signals into digital signals, and then transmit them to the controller P. The controller P can process these digital signals, such as using these digital signals to fit smooth curves, respectively and calculate the ion/virus concentration by substituting the acquired ADC signal into the corresponding curve equation. Then, the controller P can output a sensing result in response to aforesaid sensing signals. The wireless sensing data reading module 160 may wirelessly transmit the sensing result to an electronic device E through the transmitter antenna 164, in which the electronic device E may be, for example, a smart phone with a display as shown in the FIGS. 1A, 9, and 10. Thus, concentration data of the ions/virus may be presented on the display of the electronic device E, and water quality superiority or disease risk may be evaluated by an user and displayed based on this data.

Figure 10:
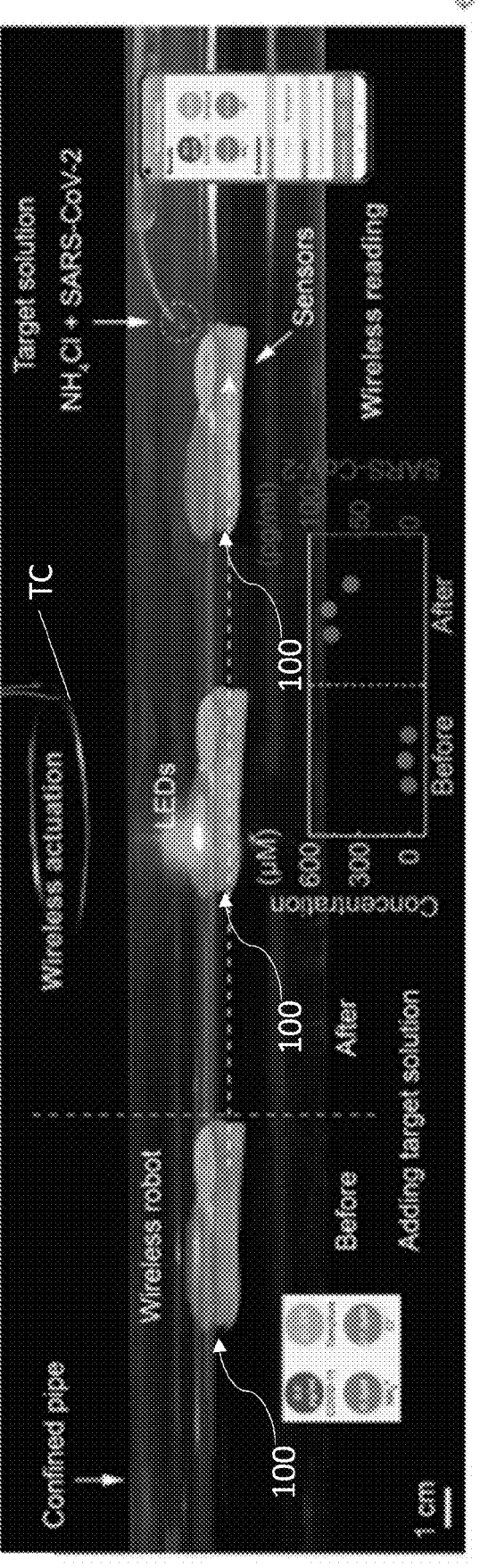
FIG. 10 shows a demonstration of a robotic device according to an embodiment of the present disclosure in a confined pipe.

FIG. 10 shows a demonstration of a robotic device 100 according to an embodiment of the present disclosure in a confined pipe.

Referring to FIG. 10, the robotic device 100 is placed in a confined plastic pipe to mimic the pipelines that is difficult-to-reach for sampling in situ to test this robotic device's 100 performance. After filling tap water in the confined plastic pipe, the robotic device 100 may be placed inside. A thin plastic tube is used to drop the target solution (e.g., 10 mM $NH_4Cl$ and 1 ng/mL SASR-CoV-2 spike protein). Firstly, when the robotic device 100 is stationary at one end of the pipe with tape water, a group of sensing data was read and displayed on graphical user interface (GUI) of the electronic device E as the comparative data. Then, 1 mL target solution is dropped into the confined pipe and diffused. After that, the robotic device 100 is actuated to the target-solution area by the RF wireless power P provided by the transmitter coil TC. As the robotic device 100 enters the electromagnetic field of the electronic device E, the electronic device E can send a reading command to the NFC circuit 162. The NFC circuit 162 would respond to the reading command, and power the sensing module 150. Then, the sensing module 150 can sense a characteristic (e.g., water quality or temperature) of an aquatic environment, or detect a living body or a bio-like structure in the aquatic environment, so as to obtain at least one sensing electrical signal. The electronic device E can receive the sensing result (sensing data) from the transmitter antenna 164. The sensing result can be shown through the GUI/display. This robotic device 100 can monitor the water environment.

Figure 11:
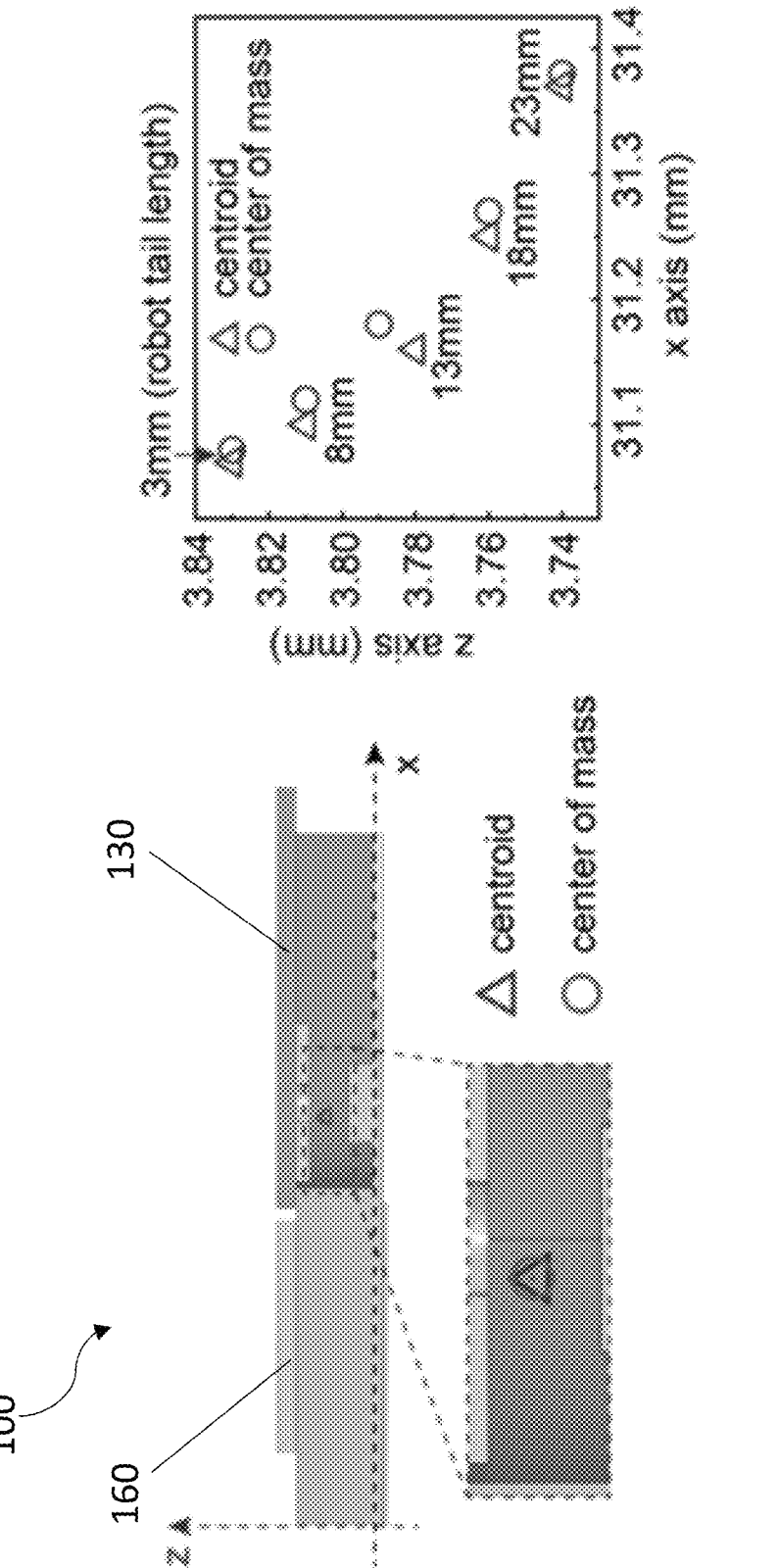
FIG. 11 depicts a cross-sectional view of the robotic device in the FIGS. 1A and 1B with tail length 8 mm and coordinate position of the centroid and center of mass for the robotic device with different tail lengths.

FIG. 11 depicts a cross-sectional view of the robotic device 100 in the FIGS. 1A and 1B with tail length 8 mm and coordinate position of the centroid and center of mass for the robotic device 100 with different tail lengths.

Referring to FIG. 11, a FEA software Ansys Mechanical can be used to design the robot structure of the robotic device 100 for the coincidence of centroid and center of mass. The shapes and sizes of the support, vibrable tail portion 120 and the sensor module 150 are well designed and the placement arrangement of the wireless power receiving module 130, the wireless sensing data reading module (i.e., NFC module), an actuation coil 142, and the magnet element is optimized in multiple iterations, so that the centroid and center of mass could well matched. Such a design can assist the robotic device 100 swim smoothly and ensures that the posture of the robotic device 100 could remain steady during its swimming motion.

Based on the above, in the embodiments of the present disclosure, the robotic device adopts a biomimetic design, such as fish-like shape design, so as to adapt the movement in the aquatic environment. The robotic device is a wireless, battery-free, goldfish-sized soft robot with highly integrated, multimodal sensing and monitoring in temperature, water quality and SARS-CoV-2 virus. This bio-inspired robotic device could swim smoothly in a confined pipe with its soft tail exhibiting a periodic oscillation to mimic the tail-beating behavior of aquatic animals, such that the robotic device can operate and perform monitoring tasks in narrow or confined pipes. Benefit from an integrated wireless electrochemical sensing system, this robotic device with a multifunctional sensing system can successfully performs the temperature monitoring, the ion content, and SARS-CoV-2 contamination's monitoring, and the synchronized data can be wirelessly transmitted to and displayed by a smartphone.

The functional units and modules of the devices and methods in accordance with the embodiments disclosed herein may be implemented using computing devices, computer processors, or electronic circuitries including but not limited to application specific integrated circuits (ASIC), field programmable gate arrays (FPGA), microcontrollers, and other programmable logic devices configured or programmed according to the teachings of the present invention. Computer instructions or software codes running in the computing devices, computer processors, or programmable logic devices can readily be prepared by practitioners skilled in the software or electronic art based on the teachings of the present invention.

All or portions of the methods in accordance to the embodiments may be executed in one or more computing devices including server computers, personal computers, laptop computers, mobile computing devices such as smartphones and tablet computers.

The embodiments may include computer storage media, transient and non-transient memory devices having computer instructions or software codes stored therein, which can be used to program or configure the computing devices, computer processors, or electronic circuitries to perform any of the processes of the present invention. The storage media, transient and non-transient memory devices can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

Each of the functional units and modules in accordance with various embodiments also may be implemented in distributed computing environments and/or Cloud computing environments, wherein the whole or portions of machine instructions are executed in distributed fashion by one or more processing devices interconnected by a communication network, such as an intranet, Wide Area Network (WAN), Local Area Network (LAN), the Internet, and other forms of data transmission medium.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

What is claimed is:

1. A robotic device with a fish shape design, comprising:
a fish shape carrier portion comprising:
    a head portion; and
    a pair of side portions extending from two opposite sides of a bottom of the head portion, respectively, such that the fish shape carrier portion has a shape design that is advantageous to assist the robotic device swim or move in an aquatic environment;
a vibrable tail portion connecting to the head portion and located between the pair of side portions;
a wireless power receiving module configured to receive a wireless power and disposed on the vibrable tail portion and the side portions;
a driving module electrically coupled to the wireless power receiving module and disposed on the vibrable tail portion, wherein the wireless power receiving module transmits the wireless power to the driving module, such that the driving module enables the vibrable tail portion rotate; and
at least one functional sensor disposed at the head portion and configured to sense a characteristic of the aquatic environment, or detect a living body or a biological structure in the aquatic environment, so as to obtain at least one sensing electrical signal, wherein the wireless power receiving module further comprises:
    a receiver antenna configured for receiving the wireless power; and
    a circuit electrically coupled to the receiver antenna and the driving module, wherein the circuit is configured to modify a waveform of the wireless power, so as to transmit the modified wireless power to the driving module.

2. The robotic device of claim 1, wherein the fish shape carrier portion has a width gradually increasing and then decreasing from a top of the fish shape carrier portion to a bottom of the fish shape carrier portion.

3. The robotic device of claim 1, wherein the vibrable tail portion is spaced apart from the pair of the side portions.

4. The robotic device of claim 1, wherein the driving module further comprises:
a magnet element disposed on and making contact with the vibrable tail portion; and
an actuation coil disposed directly above the magnet element and electrically coupled to the receiver antenna through the circuit, wherein the actuation coil generates an alternative magnetic field, such that the magnet element is driven by the alternative magnetic field, thereby enabling the vibrable tail portion to vibrate.

5. The robotic device of claim 1, wherein the circuit comprises:
at least one of capacitor electrically coupled in parallel to the driving module and the receiver antenna; and
at least one of rectifiers electrically coupled in series in the circuit.

6. The robotic device of claim 5, wherein the rectifiers comprise a plurality of diodes.

7. The robotic device of claim 6, wherein the diodes are light emitting diodes.

8. The robotic device of claim 1, further comprising:
a wireless sensing data reading module electrically coupled to the at least one functional sensor, such that the functional sensor is able to transmit the sensing electrical signal to the wireless sensing data reading module, and the wireless sensing data reading module is able to wirelessly transmit the sensing result to an electronic device.

9. The robotic device of claim 8, wherein the wireless sensing data reading module is disposed at a top surface of the head portion, and the at least one functional sensor is disposed at a bottom surface of the head portion.

10. The robotic device of claim 8, the wireless sensing data reading module comprises:
an NFC circuit coupled to the one functional sensor; and
a transmitter antenna electrically coupled to the NFC circuit, wherein the NFC circuit receives the sensing electrical signal from the at least one functional sensor and then generates a sensing result according to the sensing electrical signal, wherein the transmitter antenna is adapted to wirelessly transmitted to an electronic device.

11. The robotic device of claim 10, wherein the transmitter antenna is able to receive the wireless power to power the wireless sensing data reading module.

12. The robotic device of claim 8, wherein the wireless sensing data reading module and the wireless power receiving module are bendable.

13. The robotic device of claim 1, wherein the at least one functional sensor comprises a plurality of chemical ion sensors and a biosensor.

14. The robotic device of claim 13, wherein one of the chemical ion sensors is configured to sense concentration of $NH_4^+$ ion, and another one of the chemical ion sensors is configured to sense concentration of Cl-ion.

15. The robotic device of claim 13, wherein the biosensor is configured to sense the SARS-COV-2 virus.

16. The robotic device of claim 1, wherein center of mass of the robotic device is matched to centroid of the robotic device.

17. A robotic device with a fish shape design, comprising:
a fish shape carrier portion comprising:
    a head portion; and
    a pair of side portions extending from two opposite sides of a bottom of the head portion, respectively, such that the fish shape carrier portion has a shape design that is advantageous to assist the robotic device swim or move in an aquatic environment;

a vibrable tail portion connecting to the head portion and located between the pair of side portions;

a wireless power receiving module configured to receive a wireless power and disposed on the vibrable tail portion and the side portions;

a driving module electrically coupled to the wireless power receiving module and disposed on the vibrable tail portion, wherein the wireless power receiving module transmits the wireless power to the driving module, such that the driving module enables the vibrable tail portion rotate;

at least one functional sensor disposed at the head portion and configured to sense a characteristic of the aquatic environment, or detect a living body or a biological structure in the aquatic environment, so as to obtain at least one sensing electrical signal; and a wireless sensing data reading module electrically coupled to the at least one functional sensor, such that the functional sensor is able to transmit the sensing electrical signal to the wireless sensing data reading module, and the wireless sensing data reading module is able to wirelessly transmit the sensing result to an electronic device, and wherein the wireless sensing data reading module is disposed at a top surface of the head portion, and the at least one functional sensor is disposed at a bottom surface of the head portion.

18. A robotic device with a fish shape design, comprising:
a fish shape carrier portion comprising:

a head portion; and a pair of side portions extending from two opposite sides of a bottom of the head portion, respectively, such that the fish shape carrier portion has a shape design that is advantageous to assist the robotic device swim or move in an aquatic environment;

a vibrable tail portion connecting to the head portion and located between the pair of side portions;

a wireless power receiving module configured to receive a wireless power and disposed on the vibrable tail portion and the side portions;

a driving module electrically coupled to the wireless power receiving module and disposed on the vibrable tail portion, wherein the wireless power receiving module transmits the wireless power to the driving module, such that the driving module enables the vibrable tail portion rotate; and at least one functional sensor disposed at the head portion and configured to sense a characteristic of the aquatic environment, or detect a living body or a biological structure in the aquatic environment, so as to obtain at least one sensing electrical signal, wherein the at least one functional sensor comprises a plurality of chemical ion sensors and a biosensor.

19. The robotic device of claim 18, wherein one of the chemical ion sensors is configured to sense concentration of $NH_4^+$ ion, and another one of the chemical ion sensors is configured to sense concentration of $Cl^-$ ion.

20. The robotic device of claim 18, wherein the biosensor is configured to sense the SARS-COV-2 virus.

* * * * *